US00PP10774P

United States Patent [19]

Bohr

[11] Patent Number: Plant 10,774

[45] Date of Patent: Feb. 2, 1999

[54] *HYPERICUM PERFORMATUM* PLANT NAMED 'ANTHOS'

[75] Inventor: Christine Bohr, Sangerhausen, Germany

[73] Assignee: Erfurter Samen-und Pflanzenzucht GmbH, Erfurt, Germany

[21] Appl. No.: 831,026

[22] Filed: Apr. 1, 1997

[30] Foreign Application Priority Data

Apr. 1, 1996 [DE] Germany ..... HPE-3

[51] Int. Cl.[6] ..... A01H 5/00

[52] U.S. Cl. ..... Plt./68.1

[58] Field of Search ..... Plt./68.1, 54.1

[56] References Cited

PUBLICATIONS

Huxley, Anthony, et al., "H. Perforatum", The New Royal Horticultural Society of Horticulture Dictionary of Gardening, 1992 The Stockton Press, p. 634.

*Primary Examiner*—Howard J. Locker
*Attorney, Agent, or Firm*—Christie, Parker & Hale, LLP

[57] ABSTRACT

A plant variety of *Hypericum perforatum* producing stems of about 50 to 55 cm length with good rigidity, oppositely disposed branching and scattered spotted leaves.

3 Drawing Sheets

BACKGROUND OF THE INVENTION

The present invention relates to a new and distinct variety of *Hypericum perforatum,* commonly referred to as St. John's Wort, which is the result of selective breeding in Sangerhausen, Germany. The varietal denomination of the new variety is 'Anthos'. The seed and pollen parents of the new variety are not known because it is a selection from among plants of *Hypericum perforatum* grown in a controlled planting which was discovered to possess distinctive characteristics.

SUMMARY OF THE INVENTION

Among the novel characteristics by the new variety which distinguish it from varieties of which I am aware are its production of long 2-lined stems with oppositely disposed branching, scattered spotted leaves, and star-like golden yellow flowers on cymes which, upon crushing, yield a red colored substance. The red colored substance comprises plant dyes common to many plants e.g. rutin and the like. This substance is not of special interest in connection with the new variety.

Plants of the new variety are useful in the preparation of tea. For example, the dried upper part of the plant with the flowers may be extracted in any conventional manner to produce a preparation to make tea.

Advantages of the new variety include plant growth to uniform height and bloom horizon that is substantially uniform and a blooming period that begins early. When harvesting, the uppermost 20 to 30 cm of the plants are cut off and dried. Because of the substantially uniform height and bloom, this can be done by machines in contrast to other known varieties which must be harvested by hand because of the non-uniformity of height and bloom. Another distinctive characteristic of the new variety is that the black streaks on the flower petals, visible on other varieties, are not clearly seen. Another difference is that the green leaves of the new variety display more glands that other varieties.

Asexual reproduction by vegetative cuttings of the new variety as performed in Sangerhausen, Germany, shows that the foregoing and other distinguishing characteristics come true to form and are established and transmitted through succeeding propagations.

COMPARISON WITH OTHER VARIETIES

The new variety may be compared with the variety 'Topaz' to which it is similar, but distinguishable. The following table compares growing period, height of growth and stem rigidity of 'Anthos' and 'Topaz' when grown in Sangerhausen, Germany.

| | 'ANTHOS' | 'TOPAZ' |
|---|---|---|
| GROWING PERIOD: | Beginning August in first year<br>Beginning June after 2nd year | Beginning August in first year<br>Beginning June after 2nd year |
| | No difference between 'Anthos' and 'Topaz' | |
| HEIGHT OF GROWTH: | About 50 to 55 cm<br>Height and widths tend to equalize | About 40 to 55 cm<br>Height and widths do not equalize |
| STEM RIGIDITY | Very good | Poor |

BRIEF DESCRIPTION OF ILLUSTRATIONS

The accompanying illustrations show specimens of 'Anthos', depicted in color as nearly true as it is reasonably possible to make the same in a color illustration of this character. In the illustrations:

DESCRIPTION OF THE NEW VARIETY

Figure 1:
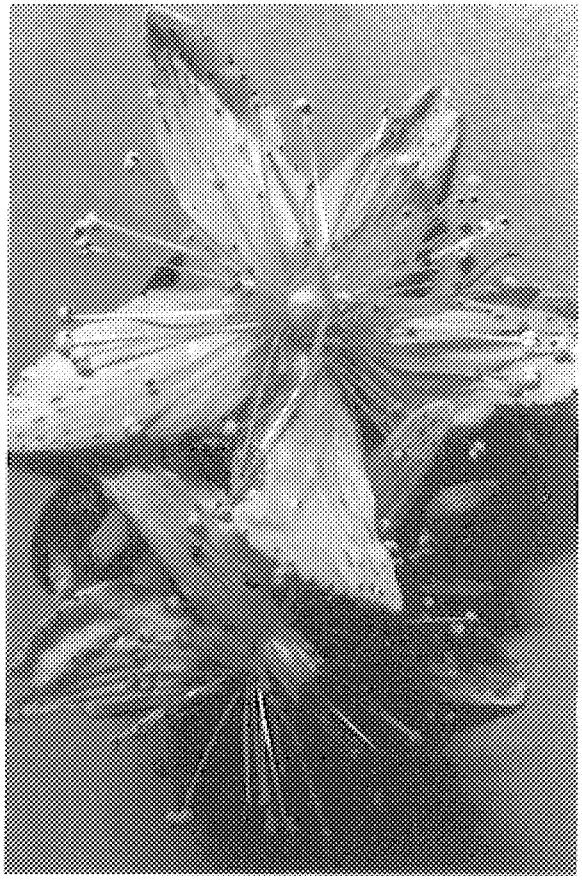
FIG. 1 is an illustration of the flower.
Figure 2:
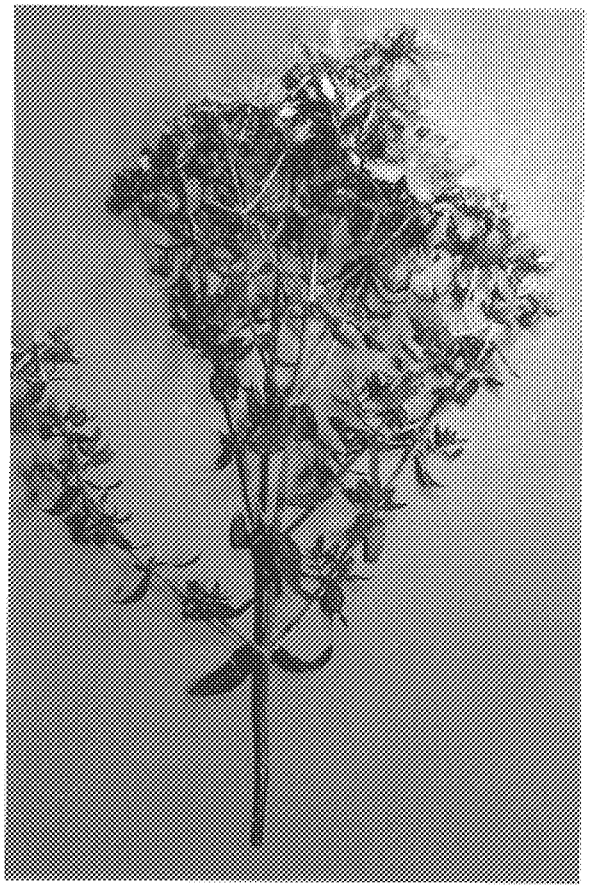
FIG. 2 is an illustration of the stem, and foliage and flowers.
Figure 3:
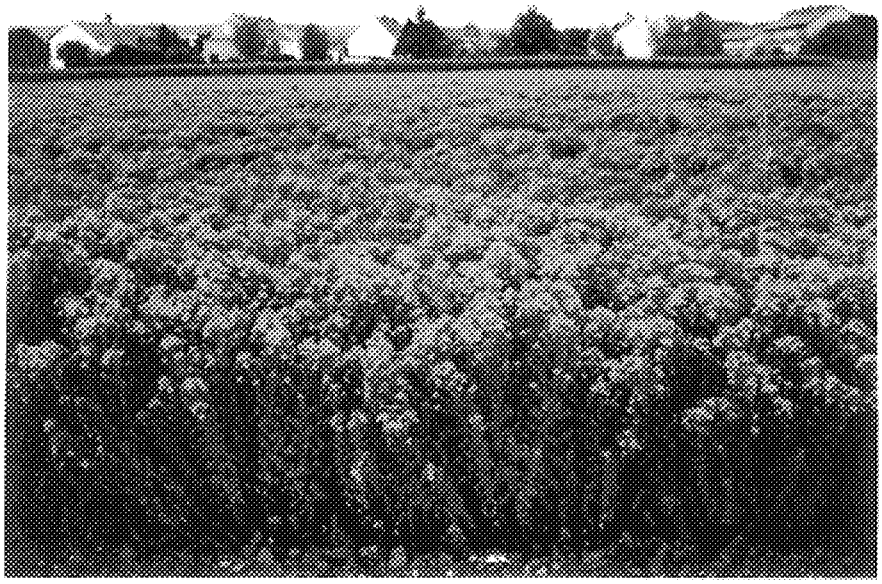
FIG. 3 is an illustration of a field of 'Anthos' grown

Parentage: Seedling.
Botanical name of family: Guttiferae.
Botanical name of variety: *Hypericum perforatum* L.
Common name: St. John's Wort.
Internal name (synonym): NLC 7.
Varietal denomination: 'Anthos'.

The following is a detailed description of the new variety from specimens grown in Sangerhausen, Germany. The specific color designations used herein are in accordance with The Royal Horticultural Society Colour Chart (R.H.S.C.C.), and refer to plate numbers in the aforementioned color chart. General terms used in reference to coloration are to be given their ordinary and accepted dictionary significance.

'Anthos' is characterized by unified growth as early as its primary year, i.e. first year of growth. The horizontal blooming aspect is very uniform and lies between 40 to 50 cm along with a corresponding stem length of about 55 cm. The new variety appears to be disease resistant inasmuch as diseases have not been observed.

*Hypericum perforatum* is a common form of St. John's Wort and is a native of Europe. St. John's Wort is now widely naturalized in the United States and is generally abundant in fields, waste places and along roadsides. 'Anthos' somewhat resembles other plants of *Hypericum perforatum* but is usually less tall, much more branched and has flowers with yellow petals and typically black-dotted only on the margins. The pistil has but three styles and the plants generally bloom between June and September in climates corresponding to Sangerhausen, Germany. Typical minimum life expectancy of St. John's Wort is about two years.

The new variety prefers sunny and dry climates and may grow as high as 50 to 60 cm in the first year and 100 to 120 cm in the second year.

In the spring, about 15 to 25 flower bearing stems are formed which have a diameter of about 4 to 5 mm at the base. The stems are hard, 2-lined and woody and comprise about 30 nodes per stem with an internode length of about 4 to 5 cm. The stems are green but about 15 to 20 cm of the base of the stem tend to have a brown colored cork-like surface. About 20 nodes have pairs of opposite branches and about 8 of the uppermost nodes bear flowers. The basal leaves enclose the nodes in pairs and are about 30 mm long and about 10 to 12 mm broad, and are lanceolate. The base of the leaves is fixed to the stem and the leaves are translucent with clearly visible veining and numerous glands. Leaf coloration is closest to R.H.S. 139B on both surfaces, with stem coloration being somewhat lighter. Sepal coloration is somewhat lighter but otherwise very similar to leaf coloration. Dark glands are present on the stems, leaves, flower petals and stamens.

The numerous sulfur yellow flowers form a corymb having a uniform bloom horizon within the upper about 20 to 30 cm of the stems. The flowers are star shaped with 5 sepals and five petals and at full bloom have a diameter of about 2 to 2.5 cm. Petal coloration is closest to R.H.S. 11A. Though there are black streaks on flower petals, they are not clearly visible. The style and stigma is divided into three parts and surrounding by numerous stamen.

The fruit is a capsule divided into three parts. Each capsule contains about 30 to 50 seeds. The seed yield is about 30 $g/m^2$ when harvested by hand.

I claim:

1. A new and distinct cultivar of *Hypericum perforatum* plant named 'Anthos', substantially as herein shown and described.

* * * * *